United States Patent [19]

Fráter et al.

[11] Patent Number: 5,113,021
[45] Date of Patent: May 12, 1992

[54] PROCESS FOR THE MANUFACTURE OF A MIXTURE OF α- AND β-IRONE

[75] Inventors: Georg Fráter, Uster; Daniel Helmlinger, Gockhausen, both of

[73] Assignee: Givaudan Corporation, Clifton, N.J.

[21] Appl. No.: 578,371

[22] Filed: Sep. 6, 1990

[30] Foreign Application Priority Data

Sep. 21, 1989 [CH] Switzerland ............ 3430/89

[51] Int. Cl.⁵ .................................... C07C 45/67
[52] U.S. Cl. ...................... 568/341; 568/361; 568/343; 568/303; 568/700
[58] Field of Search ............ 568/700, 361, 341, 343, 568/303

[56] References Cited

U.S. PATENT DOCUMENTS 3,470,261 9/1969 Eschenmoser et al. ............ 568/700
3,496,240 2/1970 Sturzenegger ..................... 568/700
3,649,694 3/1972 Eshenmoser et al. .............. 568/303

OTHER PUBLICATIONS

D. Felix et al., Chimia 18(1964) 174.
K. Kleveland et al., Acta Chem Scand. B 31 (1977) 463.
Org. Syn. 54 (1974) 11.
G. Saucy et al., Helv. Chim. Acta 50 (1967) 1158.
I. Kuwajima et al., Tet. Lett. 21 (1980) 3209.
T. F. Rutledge, "Acetylenes And Allenes", Reinhold Book Corp., N.Y. (1968) 47.

*Primary Examiner*—James H. Reamer
*Attorney, Agent, or Firm*—Robert F. Tavares; Linda A. Vag

[57] ABSTRACT

A process for the manufacture of α- and β-irone, namely the compounds of formula I, as well as novel intermediates in the process is provided.

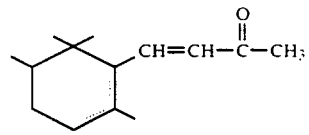

10 Claims, No Drawings

PROCESS FOR THE MANUFACTURE OF A MIXTURE OF α- AND β-IRONE

SUMMARY OF THE INVENTION

The process of the invention provides a novel method for the manufacture of α-irone, namely 4-(2,5,6,6-tetramethyl-2-cyclohexen-1-yl)-3-buten-2-one, and β-irone, namely 4-(2,5,6,6-tetramethyl-1-cyclohexen-1-yl)-3-buten-2-one, the compounds of formula I shown in Scheme I below. The process comprises isomerizing 8-(2',2'-dimethylcyclopropyl)-6-methyl-4,5-octadien-2-one, compound III, to 8-(2',2'-dimethylcyclopropyl)-6-methyl-3,5-octadien-2-one, compound II, with subsequent conversion of the latter compound to the irones. Scheme I shows the overall process of the invention.

SCHEME I

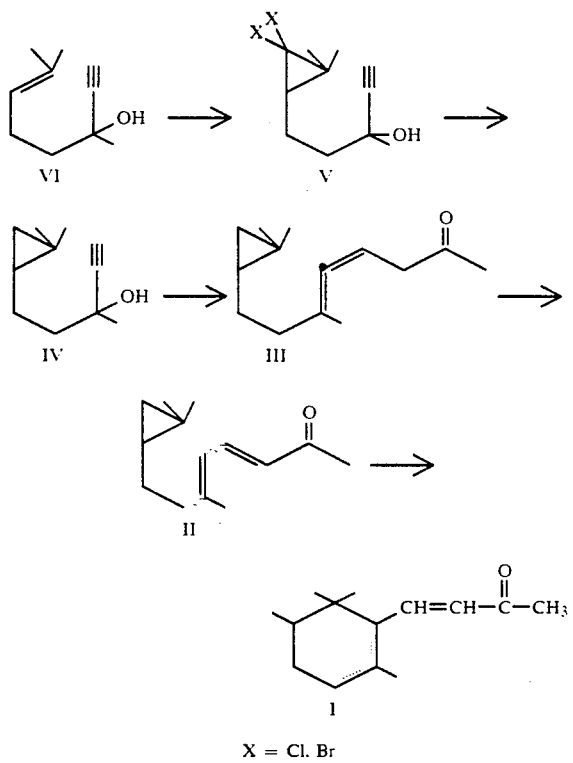

X = Cl, Br

The irones are valuable known odorant materials possessing a powerful and most pleasant violet odor. The compounds of formulas III, IV and V are novel and also form part of the present invention.

DESCRIPTION OF THE PREFERRED EMBODIMENTS

As shown in Scheme I, the first step of the overall process of the invention is the preparation of a compound of formula V namely a 5-(2',2'-dihalo-3',3'-dimethylcyclopropyl)-3-methyl-1-pentyn-3-ol, from dehydrolinalool, VI, by the cycloaddition of a dihalocarbene to the double bond of dehydrolinalool. The preferred method for the cycloaddition is the use of a haloform (chloroform or bromoform) in the presence of a strong base and a phase transfer catalyst. That this reaction proceeds only at the double bond with no effect on the triple bond is surprising, because the man skilled in the art would expect the dihalocarbene to react with both unsaturated centers. The dihalocyclopropanyl group in V is subsequently reduced to the cyclopropanyl group of compound IV, namely, 5-(2',2'-dimethylcyclopropyl)-3-methyl-1-pentyn-3-ol. Treatment with alkali metal in liquid ammonia is the preferred method for the reductive dehalogenation.

The third step in the overall process as shown in Scheme I concerns the conversion of the acetylenic carbinol group of IV to the β-keto allenic group of compound III. Treatment with an n-alkyl isopropenyl ether in the presence of a strong mineral organic acid is the preferred method for this conversion. It is surprising that in this reaction the cyclopropane ring is not affected, i.e., only the allenic ketone III, 8-(2',2'-dimethylcyclopropyl)-6-methyl-4,5-octadien-2-one, is formed as the reaction product, although the skilled researcher would have expected opening of the cyclopropane ring with strong acids, e.g. protic acids such as sulfonic acids. The allenic ketone is subsequently isomerized to the conjugated ketone II, namely 8-(2',2'-dimethylcyclopropyl)-6-methyl-3,5-octadien-2-one, using either an acid or a base as a catalyst. If an acid is used it is preferred to use a strong acid in the presence of a solvent. If a base is used to effect the isomerization it is preferred to use a alkali metal hydroxide in alcohol.

The conjugated ketone II is usually obtained as the mixture of isomers shown below.

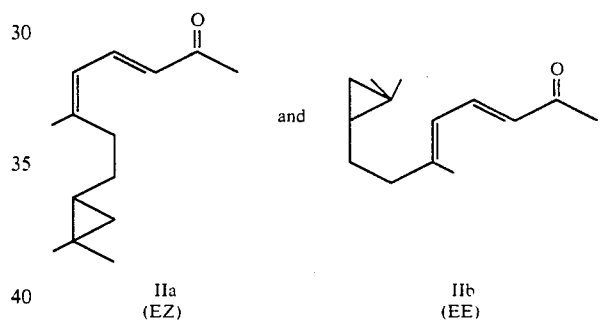

IIa (EZ)    IIb (EE)

In order to produce in the irone mixture I the highest possible amount of cis-α-irone, the perfumistically most valuable isomer, III is preferably isomerized under the influence of an acid, or if the isomerization is first carried out with base, the resultant mixture is then treated with acid. In this manner a high amount of the required isomer IIb is produced.

Compound II is a known compound (U.S. Pat. No. 3,649,694). Prior to the present invention however, a practical method for producing this compound was not available. It may be cyclized to form the irones I under acidic conditions using methods known per se. Mineral acids or Lewis acids may be suitably used for the cyclization.

The following are suitable parameters for the process:

| VI→V | |
|---|---|
| Methodology | Formation of dihalocyclopropane derivatives by the cycloaddition of dihalocarbenes to dehydrolinalool, the dihalocarbenes being accessible from haloform and a strong base using the phase transfer method (see e.g. Kleveland et al., Acta Chim. Scand. B. 31 (1947) 463–468) |
| Medium | Organic/aqueous-alkaline (chloroform, bromoform), haloform/concentrated aqueous alkalis phase transfer catalysts, e.g. trialkyl- |

| VI→V | |
|---|---|
| | benzylammonium halides |
| Temperature | About 15-35° C., especially about 15-20° C. |
| Working-up | Extraction with chlorinated hydrocarbons, e.g. methylene chloride |

| V→IV | |
|---|---|
| Methodology | Similar to dehydrohalogenation methods known per se using alkali metals in liquid ammonia, e.g. Li, Na, Org. Synthesis 54 (1974) 11 |
| Medium | Liquid ammonia, V present dissolved in an ether, for example in diethyl ether, tetrahydrofuran, dimethoxyethane, but hexane, etc. also comes into consideration. |
| Temperature | About −40 to −30° C. |
| Working-up | Evaporation of the NH₃, addition of an alcohol, e.g. ethanol, in order to destroy the excess metal, acidification, distillation |

| IV→III | |
|---|---|
| Methodology | Similar to methods known per se for the preparation of β-ketoallenes from acetylene carbinols using vinyl ethers in the presence of strong acids at elevated temperatures (G. Saucy et al., Helv. Chim. Acta 50 (1967) 1158) |
| Medium | Petroleum ether, hexane, cyclohexane, etc. Mineral acids, e.g. sulphuric acid, phosphoric acid, etc. or strong organic acids such as p-toluenesulphonic acid, etc. Vinyl ether: n-alkyl(methyl, ethyl, etc.) isopropenyl ether |
| Temperature | about 70°-100° C., under pressure |
| Working-up | Extraction with organic solvents such as e.g. ether or methylene chloride, washing neutral |

| III→II (acidic) | |
|---|---|
| Methodology | Similar to methods known per se for the isomerization of allenes in a system of conjugated double bonds using acids. (I. Kuwajima et al. Tet. Lett. 21, (1980), 3209. T. F. Rutledge, Acetylenes and allenes, Reinhold Book Corporation (1968), 47). |
| Medium | 1. Alcohol, e.g. methanol, ethanol, etc. and/or other organic solvent such as toluene, methylene chloride, ether, dimethoxyethane, etc. Preferred: alcohol and a further organic solvent. 2. Acid: strong organic acid, e.g. p-toluenesulphonic acid, mineral acid, e.g. sulphuric acid, acidic ion exchanger, e.g. Amberlite IR 120, etc. |
| Temperature | Temperatures about room temperature are preferred. |
| Working-up | Pouring into water, extraction with organic solvent (e.g. ether), washing neutral, evaporation. |

| III→II (basic) | |
|---|---|
| Methodology | Similar to methods known per se for the isomerization of allenes in a system of conjugated double bonds using bases (G. Saucy, R. Marbet, Helv. Chim. Acta 50 (1968) 1158 |
| Medium | Alcohol, e.g. ethanol, methanol/strong aqueous base, e.g. about 30% to 50% NaOH, about 30% to 50% KOH, etc. |
| Temperature | About 0-10° C. |
| Working-up | Neutralization, alcohol evaporation. Extraction with ether or hexane, washing neutral, distillation. |

| II→I | |
|---|---|
| Methodology | Cyclization using acid. (D. Felix et al., Chimia 18 (1964) 174; US-PS 3,649,694; wherein all relevant process parameters are discussed) |
| Medium | Mineral acids such as sulphuric acid, phosphoric acid, mixtures of sulphuric acid and acetic acid. Lewis acids such as boron trifluoride, aluminium chloride, etc. Solvent optional, for example (diethyl) ether, benzene, toluene, methylene chloride, ethylene chloride, etc. |

The compounds of formula I can be present in the cis and trans forms (geometric isomerism in the side-chain; stereochemistry on the ring). In the case of stereochemistry on the ring both forms are intended to be embraced and in the case of isomerism in the side-chain the trans form is intended to be embraced. In the case of the compound of formula II the formula is intended to embrace the trans form in the 3-position and the cis and trans forms in the 5-position.

The irone is obtained as a mixture of cis α-, trans α- and β-irone. The individual irones can be represented by the following formulas:

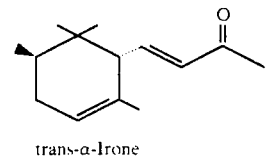

trans-α-Irone

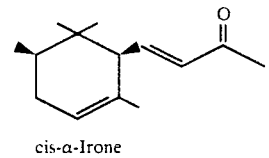

cis-α-Irone

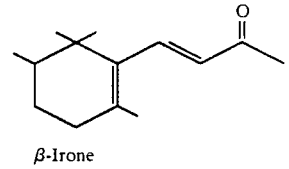

β-Irone

A separation into the individual isomers is possible, but usually is not required for use as an odorant. Suitable separation methods are, for example, distillation (e.g. using spinning band columns, Sulzer columns, etc.) or chromatography.

As mentioned earlier, a mixture having as high as possible amount of cis-α-irone is preferred.

ILLUSTRATION OF THE PREFERRED EMBODIMENTS

A number of examples are provided herein to illustrate the preferred embodiments of this invention. The examples are included for the sole purpose of illustration and should not be construed as limiting. They are intended to embrace any equivalents or obvious extensions which are known or should be known to a person skilled in the art.

EXAMPLE 1

Dehydrolinalool (400 g, 2.6 mol) and 5.26 g of triethylbenzylammonium chloride are added to a reaction flask. Chloroform (469.6 g, 3.9 mol) is added dropwise. To this solution 223.2 g (2.79 mol) of 50% sodium hydroxide solution are added dropwise within 50 minutes while cooling with ice, whereby the temperature of the reaction mixture rises to 34°. In time the initially viscous mass becomes fluid. After 21 hours of stirring and then again after 37 hours, there are added in each case within 20 minutes while cooling with ice, 160 ml of chloroform, 2.63 g of triethylbenzylammonium chloride and 111.6 g of 50% NaOH. The mixture is stirred at room temperature for a further 60 hours, poured onto ice-water, extracted with methylene chloride, washed neutral, dried over magnesium sulphate and evaporated. In this manner there are obtained 603.7 g (97%) of 5-(2',2'-dichloro-3'3'-dimethylcyclopropyl)-3-methyl-1-pentyn-3-ol.

IR (film): 3300;

H-NMR (CDCl$_3$, 400 MHz): 1.2 (s, CH$_3$—C(2')); 1.35 (s, CH$_3$—C(2')); 1.52 (s, CH$_3$—C(3)); 2.47 (s, H—C(1));

MS: 181 (13.3); 163 (6.6); 139 (29.6); 137 (26.6); 115 (9.6); 91 (15.5); 79 (29.6); 69 (97); 59 (50); 43 (100); 27 (8.1);

EXAMPLE 2

Dehydrolinalool (60.8 g, 0.4 mol), bromoform (151.6 g, 0.6 mol) and 0.8 g of triethylbenzylammonium chloride are placed in a reaction flask and 64 g of a 50% sodium hydroxide solution are added during 30 minutes. The reaction is exothermic and the mixture is therefore cooled with ice. After stirring the mixture at room temperature for 21.5 hours the same amounts of bromoform and triethylbenzylammonium chloride are again added. The reaction becomes exothermic and is cooled with ice. The mixture is left to react at 0° for a further 4 hours, poured onto ice and extracted with methylene chloride. The organic phases are washed neutral, dried and evaporated. In this manner there are obtained 109.5 g (84%) of 5-(2'2'-dibromo-3'3'-dimethylcyclopropyl)-3-methyl-1-pentyn-3-ol.

IR (film): 3300;

H-NMR (CDCl$_3$, 400 MHz): 1.22 (s, CH$_3$—C(2')); 1.4 (s, CH$_3$—C(2'); 1.54 (s, CH$_3$—C(3)); 2.48 (H—C(1)));

MS: 227 (11.8); 185 (4.4); 163 (11.8); 146 (48.1); 131 (31.1); 91 (16.2); 79 (27.4); 69 (50.3); 55 (21.4); 43 (100);

EXAMPLE 3

Ammonia, 1 l, is placed in a reaction flask. A solution of 150 g (0.63 mol) of 5-(2',2'-dichloro-3',3'-dimethylcyclopropyl)-3-methyl-1-pentyn-3-ol dissolved in 750 ml of ether is added dropwise. Sodium (62 g, 2.7 mol) in small portions is added at −30° to −35° within 2½ hours until the blue coloration persists. The ammonia is evaporated and 1.5 liters of hexane are added dropwise followed by the addition of 100 ml of ethanol. The reaction mixture is poured into a mixture of 150 ml of acetic acid in 500 g of ice, washed neutral in succession with water, saturated sodium carbonate solution, saturated sodium chloride solution, dried and evaporated. The crude product (100.2 g) is distilled. In this manner there are obtained 90.5 g (85%) of 5-(2',2'-dimethylcyclopropyl)-3-methyl-1-pentyn-3-ol.

Ammonia (54.5 ml) is placed in a reaction flask. A solution of 109.5 g (0.338 mol) of 5-(2',2'-dibromo-3',3'-dimethylcyclopropyl)-3-methyl-1-pentyn-3-ol dissolved in 415 ml of diethyl ether is added. Sodium (37.4 g, 1.662 mol) in small portions is added at −42° to −36° within 1½ hours. The mixture is stirred for 1¾ h, the ammonia is evaporated and 830 ml of hexane are added dropwise. The mixture is then stirred for 30 minutes and 60 ml of ethanol are added dropwise. The mixture is then poured into a mixture of ice and acetic acid, extracted with ether, washed neutral and evaporated. The crude product (52.9 g) is distilled at 0.06 Torr. In this manner there are obtained 27.4 g (48%) of 5-(2',2'-dimethylcyclopropyl)-3-methyl-1-pentyn-3-ol (purity 75%).

IR (film): 3300;

H-NMR (CDCl$_3$ 400 MHz): −0.1−(−0.04) (m, H—C(3)); 0.38-0.41 (m, H—C(3)); 0.44-0.54 (H—C(1)); 1.04 (s, CH$_3$—C(2)); 1.07 (s, CH$_3$—C(2)); 1.5 (s, CH$_3$—C(3)); 2.43 (s, H—C(1));

MS: 151 (0.7); 133 (6); 123 (3.5); 109 (9.8); 105 (11.9); 91 (17.6); 82 (60.5); 69 (55); 67 (59.8); 55 (57); 41 (100); 29 (17.6);

EXAMPLE 4

To a reaction flask are added 30 g (0.18 mol) of 5-(2',2'-dimethylcyclopropyl)-3-methyl-1-pentyn-3-ol, 37.8 g (0.52 mol) of isopropenyl methyl ether, 70 ml of isooctane, 40 mg of hydroquinone and 30 mg of p-toluenesulphonic acid. The mixture is heated for 24 hours while stirring (oil bath 85°). The internal temperature, which is initially at 56°, rises to 66° C. p-Toluenesulphonic acid (10 mg) is added and the mixture is heated for a further two hours (oil bath 92°). The internal temperature rises to 76° C. This crude reaction mixture can be used as such to prepare 8-(2',2'-dimethylcyclopropyl)-6-methyl-3,5-octadien-2-one or the allene may be isolated.

In order to isolate the allene, the mixture is evaporated on a rotary evaporator with the addition of sodium bicarbonate, diluted with hexane and washed with saturated sodium chloride solution and evaporated. In this manner there are obtained 37 g (99%) of crude allene, namely 8-(2',2'-dimethylcyclopropyl)-6-methyl-4,5-octadien-2-one, which can be purified further by distillation.

IR (film): 1720, 1960

H-NMR (400 MHz (CDCl$_3$)−0.107 (dd J(3'1')=5, (J(3'3')=4 Hz; H—C(3') trans to H—C(1')); 0.36 (dd, J(3'1')=8.5, J(3'$\overline{3}$')=4, H—C(3'); cis to H—C(1'); 0.44 (dddd J(1'3')=8.5, J($\overline{3}$'1')=5, J(1'8)=7, J(1'8)=7, H—C(1');

1.01 (s, CH$_3$—C(2')); 1.03 (s, CH$_3$—C(2')); 1.2-1.58 (m, H$_2$—C (8)); 1.7 (d, J=3, CH$_3$—C(6)); 2.02 (ddd, J=8, J=8, J=3, H$_2$—C(7)); 2.18 (s, CH$_3$—C(2)); 3.06 (d, J=7, H$_2$—C(3)); 5.05-5.21 (m, H—C(4));

MS: 191 (2); 163 (2); 149 (2); 133 (6); 123 (50); 107 (37.3); 95 (16); 91 (20); 79 (33.8); 67 (18.3); 55 (62.6); 43 (100); 29 (20.4);

EXAMPLE 5

The crude reaction mixture from Example 4 is allowed to flow at 0°-6° C. within 45 minutes into a solution of 2.5 ml of 30 percent sodium hydroxide solution in 32.5 ml of methanol. The mixture is stirred for 10 minutes, neutralized with 1.45 ml of acetic acid and the methanol is distilled on a rotary evaporator. The residue is washed with water, saturated sodium carbonate solution and saturated sodium chloride solution, dried, evaporated and distilled. There are obtained in this manner 3.2 g of starting material and 25.3 g (76% with respect to the reacted educt) of 8-(2',2'-dimethylcyclopropyl)-6-methyl-3,5-octadien-2-one (b.p. 83–95°/ 0.06 Torr.) as EZ and EE isomers in the ratio 2:1.

EZ isomer:

IR (film): 1590, 1625, 1665, 1690

H-NMR: −0.07 (dd J(3'1')=5, J(3'3')=4 Hz; H—C(3') trans to H—C(1')); 0.4 (dd, J(3'1')=8.5, J(3'3')=4, H—C(3') cis to H—C(1'), 0.48 (dddd J(1'3')=8.5, J(3'1')=5, J(1'8)=7, J(1'8)=7, H—C (1'); 1.02 (s, CH$_3$—C(2')); 1.07 (s, CH$_3$—C(2')); 1.47 (dd, J=7; H$_2$—(C8); 1.9 (s, CH$_3$—(C6)); 2.27 (s, CH$_3$—C(2)); 2.38 (dd, J=8, H$_2$—C(7)); 6.02 (d, J=12, H—C(5)); 6.06 (d, J=16, H—C(3)); 7.46 (dd, J=16, J=11, H—C(4));

C-NMR: 15.67 (s); 19.73 (t); 19.91 (q); 24.29 (d); 24.64 (q); 27.35 (q); 27.49 (q); 28.82 (t); 33.40 (t); 124.47 (d); 128.28 (d); 139.49 (d); 151.62 (s); 198.60 (s);

MS: 206 (2.1); 191 (3.5); 163 (5.6); 148 (4.9); 135 (6.3); 121 (11.2) 109 (74); 81 (68); 55 (100); 43 (85) 27 (19);

EE isomer: IR (film) 1590, 1630, 1670, 1690

H-NMR: 0.1 (dd) J(3'1')=5, J(3'3')=4: H—C(3') trans to H—C(1')); 0.38 (dd, J(3'1')=8.5, J(3'3')=4; H—C(3') cis to H—C(1'); 0.44 (dddd J(1'2')=8.5, J(3'1')=5, J(1'8')=7, J(1'8')=7, H—C(1'); 1.01 (s, CH$_3$—C(2')); 1.04 (s, CH$_3$—C(2')); 1.36–1.54 (m, H$_2$—C(8)); 1.9 (d, J=1 Hz, CH$_3$—C(6)); 2.21 (dd, J=8, H$^2$—C (7); 2.25 (s, CH$_3$—C(2)); H—C(5)); 6.02 (d, J=11, H—C(5)); 6.07 (d, J=16, H—C((3)); 7.42 (dd, J=16, J=11, H—C(4));

C-NMR: 15.57 (s); 17.59 (q); 19.73 (t); 19.92 (q); 24.30 (d); 27.50 (q); 27.52 (q); 28.27 (t); 41.00 (t); 123.67 (d); 128.34 (d); 139.69 (d); 151.60 (s); 198.80 (s);

MS: 206 (1.4); 191 (2.8); 163 (5.6); 148 (3.5); 135 (5.6); 122 (9.8); 109 (57); 91 (7.7); 82 (31.6); 67 (10.5); 55 (100); 43 (55); 29 (14);

EXAMPLE 6

Crude 8-(2',2'-dimethylcyclopropyl)-6-methyl-3,5-octadien-2-one (5 g, Example 5, EZ/EE=2/1) are dissolved in a mixture of 6.5 ml of methanol and 5.7 ml of toluene and 100 mg of para-toluenesulphonic acid are added. The mixture is stirred at room temperature for 17 hours. It is extracted with toluene, washed neutral with water and saturated sodium chloride solution, dried and evaporated. In this manner there are obtained 4.8 g (96%) of crude 8-(2',2'-dimethylcyclopropyl)-6-methyl-3,5-octadien-2-one, EZ/EE=4/6.

EXAMPLE 7

Crude 8-(2',2'-dimethylcyclopropyl)-6-methyl-3,5-octadien-2-one (4.5 g, Example 6, EZ/EE=4/6) are dissolved in 26 ml of toluene and then cooled to −4° C. At −4° C. to 4° C. (exothermic) boron trifluoride is introduced until the solution is saturated (uptake: about 2 g of boron trifluoride). The mixture is then, stirred under a weak stream of argon firstly at −2° C. for 10 minutes, then at 10° for 1½ hours. The mixture is extracted with ether, washed neutral with water and saturated sodium carbonate solution, dried and evaporated. In this manner there are obtained, after bulb-tube distillation, 3.4 g (75%) of a mixture of trans-α-irone, cis-α-irone and β-irone in the ratio 47/41/10.

If required, the higher-boiling β-irone can be separated from the mixture by distillation on a spinning-band column.

EXAMPLE 8

8-(2',2'-Dimethylcyclopropyl)-6-methyl-4,5-octadien-2-one, 5 g, is dissolved in a mixture of 6 ml of methanol and 6 ml of toluene, then 200 mg of p-toluenesulphonic acid are added. The mixture is stirred at room temperature for 6¾ hours. It is diluted with ether, washed neutral with saturated bicarbonate and carbonate solution and with saturated sodium chloride solution, dried and concentrated. The crude product (4.5 g) is distilled in a bulb-tube. In this manner there are obtained 4.2 g (84%) of 8-(2',2'-dimethyl-cyclopropyl)-6-methyl-3,5-octadien-2-one. EZ/EE=4/6.

We claim:

1. A process for the manufacture of 4-(2,5,6,6-tetramethyl-2-cyclohexen-1-yl)-3-buten-2-one and 4-(2,5,6,6-tetramethyl-1-cyclohexen-1-yl-3-buten-2-one which process comprises isomerizing 8-(2',2'-dimethylcyclopropyl)-6-methyl-4,5-octadien-2-one in the presence of a base or an acid to form 8-(2',2'-dimethylcyclopropyl)-6-methyl-3,5-octadien-2-one and cyclizing said 8-(2',2'-dimethylcyclopropyl)-6-methyl-3,5-ocatadien-2-one.

2. A process according to claim 1 wherein the base is an alkali metal hydroxide, and the acid is selected from the group consisting of strong organic acids, mineral acids and acidic ion exchangers.

3. A process according to claim 2 wherein the 4-(2,5,6,6-tetramethyl-1-cyclohexen-1-yl)-3-buten-2-one is separated from the 4-(2,5,6,6-tetramethyl-2-cyclohexen-1-yl)-3-buten-2-one.

4. A process according to claims 1, 2 or 3, wherein the 8-(2',2'-dimethylcyclopropyl)-6-methyl-4,5-octadien-2-one is prepared from 5-(2',2'-dimethylcyclopropyl)-3-methyl-1-pentyn-3-ol by treatment with an n-alkyl isopropenyl ether in the presence of an acid at elevated temperatures.

5. A process according to claim 4 wherein the 5-(2,2'-dimethylcyclopropyl)-3-methyl-1-pentyn-3-ol is prepared by dehalogenation of a 5-(2',2'-dihalo-3',3'-dimethylcyclopropyl)-3-methyl-1-pentyn-3-ol, wherein the dihalo group is dichloro or dibromo.

6. A process according to claim 5 wherein the dehalogenation is carried out by treatment with an alkali metal in liquid ammonia.

7. 8-(2',2'-Dimethylcyclopropyl)-6-methyl-4,5-octadien-2-one.

8. 5-(2',2'-Dimethylcyclopropyl)-3-methyl-1-pentyn-3-ol.

9. 5-(2',2'-Dichloro-3',3'-dimethylcyclopropyl)-3-methyl-1-pentyn-3-ol.

10. 5-(2',2'-Dibromo-3',3'-dimethylcyclopropyl)-3-methyl-1-pentyn-3-ol.

* * * * *